United States Patent [19]

Dunphy et al.

[11] Patent Number: 5,085,856

[45] Date of Patent: Feb. 4, 1992

[54] COSMETIC WATER-IN-OIL EMULSION LIPSTICK COMPRISING A PHOSPHOLIPID AND GLYCEROL FATTY ACID ESTERS EMULSIFYING SYSTEM

[75] Inventors: Patrick J. Dunphy, Wellingborough, England; Alan J. Meyers, Trumbull, Conn.; Richard T. Rigg, New York, N.Y.

[73] Assignee: Elizabeth Arden Co., Division of Conopco, Inc., New York, N.Y.

[21] Appl. No.: 558,140

[22] Filed: Jul. 25, 1990

[51] Int. Cl.$^5$ ............................................... A61K 7/027
[52] U.S. Cl. ........................................ 424/64; 424/63; 424/401; 424/59; 514/937; 514/873; 514/941; 514/844
[58] Field of Search ........................... 424/64; 426/662

[56] References Cited

U.S. PATENT DOCUMENTS

| 4,115,313 | 9/1978 | Lyon et al. | 252/309 |
| 4,849,132 | 7/1989 | Fujita et al. | 426/662 |
| 4,946,670 | 8/1990 | Sebag et al. | 424/64 |

FOREIGN PATENT DOCUMENTS 61-83110  4/1986  Japan .
1442426  7/1976  United Kingdom .

OTHER PUBLICATIONS

Cosmetics & Toiletries, vol. 92, Jul. 1977, p. 70.

*Primary Examiner*—Thurman K. Page
*Assistant Examiner*—D. Colucci
*Attorney, Agent, or Firm*—Milton L. Honig

[57] ABSTRACT

A cosmetic emulsion suitable for topical application to the lips comprises in addition to oil and water, an emulsifier system comprising:

i) as a first emulsifier, a phospholipid, and
   ii) a second emulsifier having a melting point of from −5° C. to 80° C.

Preferred emulsions are lipsticks and lip gloss product which can additionally comprise wax.

9 Claims, No Drawings

COSMETIC WATER-IN-OIL EMULSION LIPSTICK COMPRISING A PHOSPHOLIPID AND GLYCEROL FATTY ACID ESTERS EMULSIFYING SYSTEM

FIELD OF THE INVENTION

The invention relates to a cosmetic emulsion composition, particularly to an emulsion which is adapted to be applied to human skin, especially the lips, for depositing thereon a protective and/or therapeutic and/or coloured film. The invention is accordingly more particularly concerned with an improved emulsion lipstick having an enhanced in-use feel, moisturisation, protection and reparative properties.

BACKGROUND AND PRIOR ART

In conventional lipstick manufacture, fats and/or oils, together with pigments and/or lakes, and other non-aqueous ingredients, are usually added to a wax base which is melted to enable the ingredients to be thoroughly mixed and is then cast into moulds which, after cooling, provide lipsticks. In commercially available lipsticks, water is not usually incorporated into the lipstick formulation, and therefore, the lipstick when applied to the lips does not necessarily possess the smooth, soft attributes associated with other skin treatment products, such as skin creams, particularly those intended for moisturising the lips.

It is accordingly desirable to provide for some users a lipstick that has more of the moisturising attributes of skin products, such as those referred to above, than conventional water-free lipsticks.

It has been proposed in JP-A-61/8310 (Konuki) to incorporate water into a lipstick to achieve in use a fat/oil coating containing water on the lip surface, to provide, so it is stated, healthy, beautiful lips. Moreover, the product is said to have a soft and good feeling in use. To achieve this, dispersing agents such as cholesterol, phytosterol, phospholipids and/or saponins are employed. Also, anionic surfactants, cationic surfactants, nonionic surfactants or amphoteric surfactants may be used so that water or a solution of water-soluble substances in water can be more homogenously and stably dispersed in this type of product.

Our attempts to repeat the teaching of JP-A-61/83110 have resulted in lipsticks which, although possessing some moisturising capacity in view of the small amount of water present, still do not meet the requirements of the more discerning user, in that the products are too soft and/or do not glide easily over the lip surface during application and/or leave an imperfect film or undesirable after feel on the lip surface following application.

It is accordingly with the avoidance of these disadvantages, particularly with improving moisturisation of the lips and delivery thereto of skin care active ingredients, that this invention is concerned.

SUMMARY OF THE INVENTION

We have now discovered that by employing a very special mixture of emulsifiers, that a superior water-in-oil lipstick can be obtained which possesses none of the negative attributes of the lip products made according to the teaching of JP-A-61/83110.

DEFINITION OF THE INVENTION

Accordingly, the invention provides a cosmetic emulsion suitable for topical application to the lips, which comprises in addition to oil and water, an emulsifier system comprising:
(i) as a first emulsifier, a phospholipid; and
(ii) a second emulsifier having a melting point of from $-20°$ C. to $80°$ C.

DISCLOSURE OF THE INVENTION

The invention is concerned with an improved cosmetic emulsion, particularly a lipstick, which comprises a very special emulsifier system that imparts to the emulsion a consumer-perceivable improved in-use benefits. Preferably, the emulsion is a water-in-oil emulsion, but it is alternatively possible to provide a product form in accordance with the invention which is an oil-in-water emulsion.

The function of the special emulsifier system is not only to provide these in-use benefits, but also to aid the delivery to the skin, particularly the lips, of skin care active ingredients, as hereinafter disclosed, which can function to provide moisturisation, emolliency and other improvements.

The emulsifier system

The emulsifier system comprises, as a first emulsifier, a phospholipid, which contributes to the stability and pleasing appearance of the emulsion. Examples of three classes of phospholipids are phosphoglycerides, lysophosphoglycerides and the important but smaller group of sphingomyelins. It is also possible to employ a mixture of two or more of these phospholipids, which together would then comprise the first emulsifier.

Examples of phosphoglycerides include:
phosphatidyl choline,
phosphatidyl ethanolamine,
phosphatidyl serine,
phosphatidyl inositol,
diphosphatidyl glycerol, and
mixtures thereof.

The most preferred phosphoglyceride is that known as lecithin, particularly soyabean lecithin, which comprises a mixture of some of the above examples of specific phosphoglycerides.

Examples of lysophosphoglycerides includes:
lysophosphatidyl choline,
lysophosphatidyl ethanolamine,
lysophosphatidyl serine,
lysophosphatidyl inositol, and
mixtures thereof The amount of phospholipid normally present in the cosmetic emulsion of the invention is from 0.2 to 10%, preferably from 0.5 to 2% by weight of the cosmetic emulsion.

The emulsifier system also comprises, in addition to the phospholipid, a second emulsifier having a melting point of from $-20°$ C. to $80°$ C., preferably from $-5°$ to $50°$ C. It is also possible to employ a mixture of two or more of these second emulsifiers, which together would then comprise the second emulsifier.

Examples of the second emulsifier include derivatives of glycerol, such as:
i) monoacyl (mainly 1-substituted) glycerol, such as glyceryl monoalkanoates, in which the alkanoate group has from 2 to 20 carbon atoms, with or without one or more hydroxyl groups, and is branched or unbranched, specific examples of which are:

glyceryl caprylate
glyceryl caprate
glyceryl laurate
glyceryl myristate
glyceryl palmitate
glyceryl stearate
glyceryl isostearate or glyceryl monoalkenoates, in which the alkenoate group has from 3 to 20 carbon atoms, with or without one or more hydroxyl groups, and is branched or unbranched, and has from 1 to 4 double bonds, specific examples of which are:

glyceryl oleate
glyceryl linoleate
glyceryl ricinoleate.

ii) diacyl 1,2- or 1,3- di substituted) glycerol, such as glyceryl dialkanoates, in which the alkanoate groups each have from 2 to 20 carbon atoms, with or without one or more hydroxyl groups, and each are branched or unbranched, specific examples of which are:

glyceryl diacetate,
glyceryl dibutanoate,
glyceryl dilaurate, or glyceryl dialkenoates, in which the alkenoate groups each have from 3 to 20 carbon atoms, with or without one or more hydroxyl groups, and each are branched or unbranched, and have from 1 to 4 double bonds, a specific example of which is:

glyceryl dioleate
glyceryl dilinoleate.

iii) polyglyceryl esters, in which the acyl groups each have from 2 to 20 carbon atoms, with or without one or more hydroxyl groups, are each branched or unbranched, a specific example of which is polyglyceryl ricinoleate.

Particularly preferred examples of the second emulsifiers are:

glyceryl caprate: melting point 40° C.,
glyceryl laurate: melting point 51° C.,
glyceryl myristate: melting point 61° C.,
glyceryl palmitate: melting point 69° C.,
glyceryl stearate: melting point 75° C.,
glyceryl oleate: melting point 35° C.,
glyceryl linoleate: melting point 12° C.,
glyceryl isostearate: melting point 5° C.,
glyceryl dilinoleate: melting point −3° C.,
glyceryl dicaprate: melting point 44° C., The melting points quoted above are applicable to the most stable, highest melting forms in each case.

The second emulsifier can comprise one or more pure glycerides, but it is usually more convenient to employ glycerides derived from natural oils such as vegetable or seed oils, examples of which are sunflower seed oil, soyabean oil, palm kernel oil and palm oil. Particularly preferred are monoglycerides of sunflower seed oil and of palm oil, and mono-and di-glycerides of soyabean oil.

Further examples of the second emulsifier include esters of fatty alcohols with a hydroxy acid, such as glyceryl citrate, cetyl citrate and cetyl lactate (having melting point of 24° C.).

The amount of the second emulsifier normally present in the cosmetic emulsion of the invention is from 0.2 to 10%, preferably from 0.5 to 5% by weight of the cosmetic emulsion.

It is apparent that cosmetic emulsions containing less than 0.2% by weight of either the first or the second emulsifier can be unstable and lack the desirable pleasing appearance attributable to the presence of a higher level of either of these emulsifiers. Furthermore, cosmetic emulsions containing more than 10% by weight of either emulsifier usually do not exhibit greater stability, and indeed may be less stable than those containing these emulsifiers in amounts within the defined range. Also, such a high level of the emulsifiers, ie. >10% by weight of each, can detract from the desirable pleasing appearance and other properties of the emulsion.

The oil

The cosmetic emulsion of the invention also comprises an oily ingredient, hereinafter referred to as an "oil" which together with water and the emulsifier system, forms a water-in-oil or oil-in-water emulsion.

A chosen oil will normally be liquid at room temperature (i.e. 20° C.), and can comprise a single oil or a mixture of two or more oils. Example of suitable oils include:

caprylic triglycerides
capric triglycerides
isostearic triglycerides
adipic triglycerides
propylene glycol myristyl acetate
lanolin oil
polybutene
isopropyl palmitate
isopropyl myristate
diethyl sebacate
diisopropyl adipate
hexadecyl stearate
cetyl oleate
oleyl alcohol
hexadecyl alcohol
wheatgerm oil
hydrogenated vegetable oils
petrolatum
modified lanolins
branched-chain hydrocarbons, alcohols and esters
castor oil
corn oil
cotton seed oil
olive oil
palm kernel oil
rapeseed oil
safflower seed oil
jojoba oil
evening primrose oil
avacado oil
mineral oil
volatile and non-volatile silicone oils The amount of the oil normally present in the cosmetic emulsion of the invention is from 2 to 97%, preferably 30 to 90% by weight of the cosmetic emulsion.

Water

The cosmetic emulsion of the invention also comprises water which forms the basis of the aqueous phase of the emulsion and provides a solvent for any water-soluble ingredients present in the cosmetic emulsion.

The amount of water present in the cosmetic emulsion of the invention is from 1 to 95%, the preferred amount depending on the product form of the cosmetic emulsion.

Wax

The cosmetic emulsion of the invention can optionally also comprise one or more waxy ingredients, hereinafter referred to as a "wax".

Examples of waxes include:
candelilla wax
ozokerite wax
carnauba wax
beeswax
spermaceti
cetyl alcohol
stearyl alcohol
lanolin.

The amount of wax when present in the cosmetic emulsion of the invention is up to 25%, usually from 1 to 25% and, preferably from 5 to 20% by weight of the cosmetic emulsion.

Skin care active ingredients

The cosmetic emulsion of the invention can optionally also comprise skin care active ingredients which can improve the quality of skin, particularly dry or damaged skin especially the lips, or which can possess a therapeutic or pharmaceutical benefit. By way of example, the following skin care active ingredients can be employed, in the amounts stated, in lip treatment emulsions of the invention, especially in lipsticks.

|  | % w/w/ |
| --- | --- |
| Zinc oxide | 1 to 2 |
| β-glycyrrhetic acid | 0.1 to 1 |
| camomile oil | 0.1 to 1 |
| ginko biloba extract | 0.1 to 1 |
| pyroglutamic acid, salts or esters | 0.5 to 5 |
| sodium hyaluronate | 0.1 to 5 |

For the treatment of spots, pimples and acne comedones, additional therapeutically or pharmaceutically active ingredients can be employed. Examples are:

|  | % w/w |
| --- | --- |
| 2 hydroxyoctanoic acid | 0.5 to 5 |
| sulphur | 1 to 10 |
| salicylic acid | 1 to 3 |
| carboxymethyl cysteine | 0.1 to 5 |

The amount of skin care active ingredients when present in the cosmetic emulsion of the invention will normally be from 0.0001 to 10% by weight of the cosmetic emulsion. In general terms it can be stated that the amount of any skin care active ingredient can be that which is conventionally employed in products intended for topical application to human skin.

Other ingredients

The cosmetic emulsion of the invention can optionally also comprise other ingredients as conventionally employed in lipsticks or other lipcare products.

Examples of other ingredients include perfumes, antioxidants, colourants such as staining dyes and pigments, humectants, germicides, sunscreens, and lipid materials.

Particularly preferred pigments, when present, include calcium, barium and aluminium lakes, iron oxides, titanium dioxide, and mica.

Particularly preferred humectants include glycerol, sorbitol and other polyols.

Particularly preferred germicides include Triclosan.

Particularly preferred sunscreens include octyl methoxycinnamate and butyl methoxydibenzoylmethane.

Particularly preferred lipid materials include ceramides and liposomes.

Product form

The cosmetic emulsion of the invention can take the form of a solid stick or a lip gloss or cream which can be applied to the lips with a suitable applicator.

Preferably, the emulsion is a water-in-oil emulsion, the amount of each phase present being governed by the form of the product itself.

For example, when the cosmetic emulsion is a stick, the aqueous phase will usually form from 2 to 50%, preferably from 5 to 15% by volume and the oily phase, including wax ingredients, will form from 98 to 50, preferably 95 to 85% by volume of the emulsion.

A particularly preferred embodiment of the invention is a water-in-oil emulsion lipstick comprising:
i. from 30 to 97% by weight of oil
ii. from 1 to 25% by weight of wax
iii. from 1 to 20% by weight of water
iv. a sufficient amount of an emulsifier system comprising:
   a. from 0.2 to 10% by weight of a phospholipid, and
   b. from 0.2 to 10% by weight of a glyceryl monoalkenoate, in which the alkenoate group has from 3 to 20 carbon atoms; and
v. a sufficient amount of pigment.

When the emulsion is a lip gloss or cream, the aqueous phase will normally form from 2 to 95%, preferably from 2 to 40% by volume of the emulsion, and the oily phase, usually including wax, will form from 98 to 5%, preferably from 90 to 60% by volume of the emulsion.

Use of the Emulsion

The cosmetic emulsion of the invention is ideally suited for use in treating the lips, especially for applying to the lips a permanent or semi-permanent colour, ideally with a gloss or lustre finish. The emulsion can also be used in treating the lips with a skin care agent for protection against exposure to adverse weather, including the wind and the rain or exposure to excessive doses of sunlight.

The cosmetic emulsion for example in the form of a stick, a gloss, salve or cream, can accordingly be applied to the lips in the traditional manner using a convenient holder or applicator to provide a decorative and/or protective film thereto.

EXAMPLES

The invention is further ilustrated by the following examples.

EXAMPLE 1 a cosmetic emulsion lipstick in accordance with the invention contained the following ingredients:

| Ingredient | % w/w |
| --- | --- |
| A. Oily Phase | |
| Oil | |
| caprylic/capric triglyceride | 5.8 |
| propylene glycol myristyl ether acetate | 6.0 |
| lanolin oil | 2.5 |
| polybutene | 0.8 |

| Ingredient | % w/w |
|---|---|
| caprylic/capric/isostearic/adipic triglyceride | 7.0 |
| isopropyl palmitate | 11.6 |
| Wax | |
| candelilla wax | 6.6 |
| ozokerite wax | 2.5 |
| carnauba wax | 0.4 |
| beeswax | 4.1 |
| lanolin | 7.0 |
| Emulsifier system | |
| phospholipid, namely soyabean lecithin | 1.0 |
| glyceride, namely Hymono 8903* | 3.5 |
| B. Aqueous phase | |
| glycerol | 5.0 |
| water | 5.0 |
| C. Pigments dispersed in castor oil | |
| titanium dioxide | 4.7 |
| colourants | 7.0 |
| castor oil | 19.5 |

*Hymono 8903 is distilled monoglyceride (>90%) based on palm oil.

The lipstick having the above formulation was manufactured as follows:

1. The combiend wax, oil and emulsifier which comprise the oily phase (A) were heated and stirred in a sealed vessel to a temperature of 90° C., until the mass had melted.
2. The melt so obtained was then cooled to 75°-80° C. and stirred under vacuum to remove air.
3. The aqueous phase comprising water and water-soluble ingredients (B) was heated to a temperature of 75°-80° C. and then slowly added, with mixing, to the molten oily pahse (A) and the mixture homogenised for from 5 to 10 minutes.
4. Pigments and fragrance dispersed in castor oil (C) were finally added and the water-in-oil emulsion so formed was further deaerated prior to cooling.
5. The deaerated emulsion was finally poured into moulds and cooled to form lipsticks.

EXAMPLES 2 to 12

Examples 2 to 12 illustrate further cosmetic emulsion lipsticks according to the invention. In each example the emulsifier was varied, while the remaining ingredients remained unchanged.

The phospholipid emulsifier employed in each case was as follows:

| Example No. | Phospholipid | % w/w |
|---|---|---|
| 2 | Soya lecithin | 1 |
| 3 | Soya lecithin | 1 |
| 4 | Soya lecithin | 1 |
| 5 | Soya lecithin | 1 |
| 6 | Soya lecithin | 1 |
| 7 | Soya lecithin | 0.5 |
| 8 | Soya lecithin | 2 |
| 9 | Soya lecithin | 1 |
| 10 | Soya lecithin | 1 |
| 11 | Lyso-soya lecithin | 1 |
| 12 | Phosphatidyl choline-enriched soya lecithin | 1 |

The glyceride emulsifier employed in each case was as follows:

| Example No. | Glyceride | % w/w |
|---|---|---|
| 2 | Sunflower oil monoglyceride | 3.5 |
| 3 | Glyceryl isostearate | 3.5 |
| 4 | Glyceryl caprate | 3.5 |
| 5 | Sunflower oil monoglyceride | 2.5 |
| 6 | Sunflower oil monoglyceride | 5 |
| 7 | Sunflower oil monoglyceride | 3.5 |
| 8 | Sunflower oil monoglyceride | 3.5 |
| 9 | Soyabean oil mono/diglyceride | 3.5 |
| 10 | Polyglyceryl ricinoleate | 3.5 |
| 11 | Sunflower oil monoglyceride | 3.5 |
| 12 | Sunflower oil monoglyceride | 3.5 |

EXAMPLE 13

A cosmetic emulsion lip gloss in accordance with the invention contained the following ingredients:

| | % w/w |
|---|---|
| A) Oily phase | |
| Oil | |
| polybutene | 34 |
| lanolin oil | 20 |
| preservative | 1 |
| PPG-5-lanolin wax | 13 |
| Wax | |
| lanolin wax | 13 |
| Emulsifier system | |
| soya lecithin | 1 |
| sunflower oil monoglycerides | 3.5 |
| B) Aqueous phase | |
| glycerol | 5 |
| water | 5 |
| C) Pigments dispersed in lanolin oil (as above) | |
| titanium dioxide | 3 |
| colourants | 1.5 |

EXAMPLES 14 and 15

Examples 14 and 15 illustrate further cosmetic emulsion lip gloss products according to the invention. In each case, the formulation was similar to that of Example 13 except that the aqueous phase or the emulsifier system was varied as follows:

In Example 14, the aqueous phase formed 20% w/w of the formulation (1:1 glycerol:water) with all other ingredients, except the emulsifier system being reduced proportionately.

In Example 15, the emulsifier was 1.0% soya lecithin +3.5% distilled monoglyceride (>90%) based on palm oil.

EXAMPLE 16

This example illustrates a further cosmetic emulsion lipstick according to the invention. The formulation and processing were identical to Example 1 except that the aqueous phase was varied as follows:

In Example 16, the aqueous phase included 2.5% by weight, in terms of the finished product, of a lecithin liposome ingredient based on dispersed and included sodium hyaluronate. The liposome ingredient contained 0.1% by weight sodium hyaluronate and 10% by weight lecithin and had a maximum particle size of 100 nm.

We claim:
1. A cosmetic water-in-oil emulsion lipstick which comprises:
   i) from 0.2 to 2% by weight of a first emulsifier which is a phospholipid selected from the group consist- ing of: phosphoglycerides, lysophosphoglycerides, sphingomyelins and mixtrues thereof;
ii) from 0.2 to 10% by weight of a second emulsifier selected from the group consisting of glycerol monoalkanotes, glycerol monoalkenotes, glycerol dialkanotes, glycerol dialkenoates and mixtures thereof;
iii) from 2 to 97% by wieght of oil liquid at room temperature;
iv) from 1 to 25% by weight of wax;
v) an effective amount of water to mositurize lips; and
iv) a sufficient amount of a pigment for coloring lips.

2. The cosmetic emulsion of claim 1 further comprising a skin care active ingredient selected from the group consisting of pyroglutamic acid, hyaluronic acid, salts of said acids and mixtures thereof.

3. The cosmetic emulsion of claim 1, wherein the phosphoglyceride is selected from the group consisting of:
phosphatidyl choline,
phosphatidyl ethanolamine,
phosphatidyl serine,
phosphatidyl inositol,
diphosphatidyl glycerol, and
mixtures thereof.

4. The cosmetic emulsion of claim 1 wherein the phospholipid is a lecithin.

5. The cosmetic emulsion of claim 1, wherein the lysophosphoglyceride is selected from the group consisting of:
lysophosphatidyl choline,
lysophosphatidyl ethanolamide,
lysophosphatidyl serine,
lysophosphatidyl inositol, and
mixtures thereof 6. The cosmetic emulsion of claim 1, wherein the second emulsifier is a glyceride selected from the group consisting of:
i) glyceryl monoalkanoates, in which the alkanoate group has from 2 to 20 carbon atoms;
ii) glyceryl monoalkenoates, in which the alkenoate group has from 3 to 20 carbon atoms; and
iii) mixtures thereof.

7. The cosmetic emulsion of claim 1, wherein the second emulsifier is a diglyceride selected from the group consisting of:
i) glyceryl dialkanoates, in which the alkanoate groups each have from 2 to 20 carbon atoms;
ii) glyceryl dialkenoate, in which the alkenoate groups each have from 3 to 20 carbon atoms; and
iii) mixtures thereof.

8. A cosmetic water-in-oil emulsion lipstick which comprises:
i) from 30 to 97% by weight of oil liquid at room temperature;
ii) from 1 to 25% by weight of wax;
iii) from 1 to 20% by weight of water;
iv) a sufficient amount of an emulsifier system comprising:
a. from 0.2 to 2% by weight of a phospholipid, and
b. from 0.2 to 10% by weight of a glyceryl monoalkanoate or monoalkenoate, in which the alkanoate or alkenoate group has from 8 to 20 carbon atoms; and
v) a sufficient amoutn of pigment for coloring lips.

9. The cosmetic emulsion of claim 1, wherein the water forms from 1 to 95% by weight of the emulsion.

* * * * *

UNITED STATES PATENT AND TRADEMARK OFFICE
CERTIFICATE OF CORRECTION

PATENT NO. : 5,085,856

DATED : February 4, 1992

INVENTOR(S) : Patrick J. Dunphy, Alan J. Meyers, Richard T. Rigg

It is certified that error appears in the above-identified patent and that said Letters Patent is hereby corrected as shown below:

Column 9, lines 5-6, should read --noalkanoates, glycerol monoalkenoates, glycerol dialkanoates, glycerol dialkenoates and mixtures--;

line 8, change "wieght" to --weight--; and line 11, change "mositurize" to --moisturize--.

Column 10, line 31, change "amoutn" to --amount--.

Signed and Sealed this

Third Day of August, 1993

Attest:

MICHAEL K. KIRK

*Attesting Officer*     *Acting Commissioner of Patents and Trademarks*